United States Patent
Pfeiffer et al.

(10) Patent No.: US 6,427,352 B1
(45) Date of Patent: Aug. 6, 2002

(54) DEVICE TO ALIGN AND MOUNT A WORKPIECE ON A HOLDING DEVICE

(75) Inventors: Joachim Pfeiffer, Bensheim; Thomas Hasenzahl, Darmstadt; Franz Basler, Laudenbach, all of (DE)

(73) Assignee: Sirona Dental Systems GmbH, Bensheim (DE)

(*) Notice: Subject to any disclaimer, the term of this patent is extended or adjusted under 35 U.S.C. 154(b) by 0 days.

(21) Appl. No.: 09/558,212

(22) Filed: Apr. 26, 2000

(30) Foreign Application Priority Data

May 7, 1999 (DE) .......................... 199 21 264

(51) Int. Cl.[7] .............................................. A61C 19/04
(52) U.S. Cl. ............................ 33/513; 33/549; 33/613; 33/645; 356/244
(58) Field of Search ..................... 33/513, 549, 1 BB, 33/613, 645, 533, 573, 644, 547; 356/244; 359/424, 427, 428, 383, 392, 808, 809, 811

(56) References Cited

U.S. PATENT DOCUMENTS

| 1,412,380 A | * | 4/1922 | Weston .................... 33/613 |
| 2,803,986 A | * | 8/1957 | Choiniere et al. .......... 359/503 |
| 3,166,628 A | * | 1/1965 | Walter ..................... 359/392 |
| 4,265,023 A | * | 5/1981 | Frost et al. ............... 33/502 |
| 5,175,644 A | * | 12/1992 | Dosaka .................... 359/392 |
| 5,583,691 A | * | 12/1996 | Yamane et al. .............. 359/393 |
| 5,812,310 A | * | 9/1998 | Stewart et al. ............. 359/392 |
| 6,237,242 B1 | * | 5/2001 | Woytassek et al. ........... 33/613 |

FOREIGN PATENT DOCUMENTS

EP          0455855          4/1995

OTHER PUBLICATIONS

Mikroskopie in Nacre. Chem. Tech. Lab. 38 (1990), No. 10, pp. M2–M23.

* cited by examiner

Primary Examiner—Diego Gutierrez
Assistant Examiner—Madeline Gonzalez
(74) Attorney, Agent, or Firm—Dykema Gossett PLLC

(57) ABSTRACT

Holding device for aligning and mounting a workpiece in an apparatus includes a receiving opening (6) provided for the holding device (20; 30), means (7) for positioning the holding device disposed in the receiving opening (6) for determination of the position of the holding device in relation to the receiving opening, wherein the holding device (20; 30) is connected with a workpiece carrier (21; 31), wherein the workpiece carrier (21; 31) is adjustable relative to the holding device, and wherein optical means (8; 11–17) are provided for viewing of the workpiece and thereby alignment of the workpiece on the holding device is performed.

11 Claims, 4 Drawing Sheets

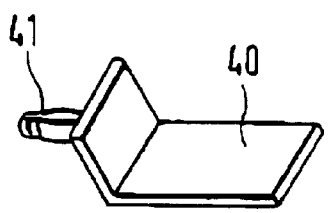
FIG.5
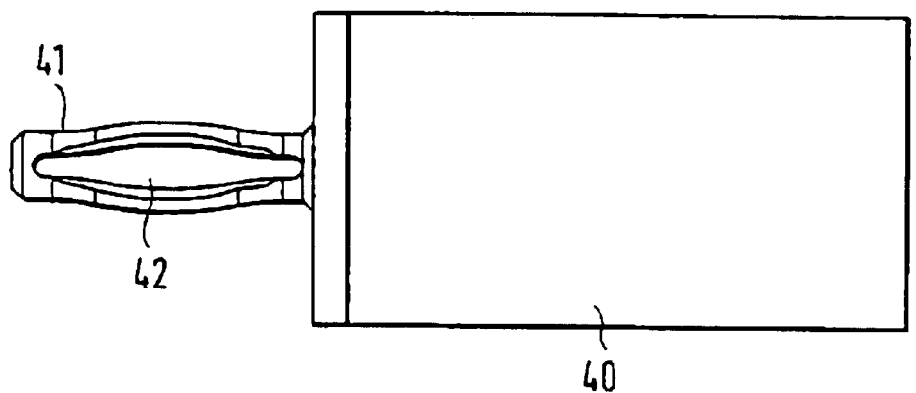
FIG.6
FIG.7
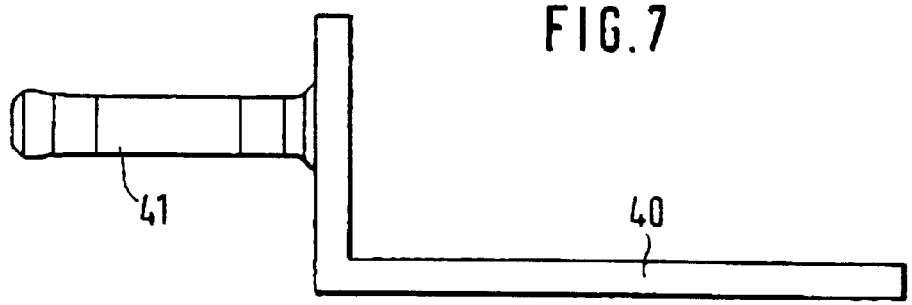

DEVICE TO ALIGN AND MOUNT A WORKPIECE ON A HOLDING DEVICE

BACKGROUND OF THE INVENTION

1. Field of the Invention

The invention relates to a device to align and mount a workpiece on a holding device. Teeth or sets of teeth are considered as workpieces, which must be aligned and mounted on the holding device for the purpose of measuring from one specific direction.

The device according to the invention is used particularly in the preparation for optical measurements of impressions or models of sets of teeth. The measurement data obtained from the measuring is further processed by dental CAD/CAM procedures. Hereby it is necessary to firmly mount models or impressions in an apparatus for optical measuring. In optical measuring one always measures from one single viewing direction or several measurements are taken from various specified viewing directions one after the other. There is an interest to keep the number of (viewing) directions to a minimum. This is achieved in that the measurement is taken from a favorable direction. It is especially advantageous during measuring of models of ready-prepared teeth and manufacturing of dentures to measure from the more recent insertion direction of the dental prosthesis that is to be produced. Measuring of the model only is sufficient in this case to obtain all important data. There is therefore the necessity to fasten the model in the measuring apparatus in such a manner that it may be measured from exactly that advantageous direction.

2. The Prior Art

EP 0 455 855 B1 discloses a method for producing medical, particularly dental prosthetic fitting bodies wherein a positive or negative model is produced. The model is subsequently inserted into a receiving device of a processing apparatus and is then measured tri-dimensional with the aid of a measuring device. Thereby it is possible that the model can be simultaneously rotated and moved linear during measuring whereby the model may be measured from various viewing directions.

It is the object of the present invention to make an accurate measurement possible even when a rotational movement of the workpiece is not desired for some reason or is not possible for the purpose of measuring. In addition, it is necessary that the workpiece to be measured on the holding device is aligned in a suitable manner so it can be later received in the measuring apparatus.

SUMMARY OF THE INVENTION

The device to align and mount a workpiece on a holding device, according to the invention, is provided with a receiving opening for the holding device whereby means for positioning relative to the receiving device are disposed on the receiving opening. The holding device is connected with a workpiece carrier. The workpiece carrier is adjustable against the holding device and there are optical means proposed for viewing of the workpiece.

With such type of a device alignment may be performed outside the measuring device of the workpiece, which is disposed on the workpiece carrier, in relation to the holding device whereby the direction of the holding device may be clearly determined. This alignment is performed according to the necessary criteria for the measurement. Should teeth be the workpiece to be measured, which are to be fitted into a fitting body, then the measurement direction is preferably the insertion direction of the fitting body.

The optical means are advantageously disposed on an axis perpendicular to the center axis of the holding device since in this case the measuring device is also designed in this manner. The axis of the optical means in relation to the holding device is preferably the same as the axis of the measurement.

Should the workpiece have recesses, then the workpiece can be aligned in such a way that measurement of a recess is made possible as long as there is no undercutting.

To avoid tilting during viewing of the workpiece by optical means, it is advantageous if at least two cooperating alignment aids are provided. Concentric circles arranged at a distance to one another along the center axis of the optical means are especially suitable as alignment aids. Of course, cross hairs of similar alignment aids may be provided here also.

As optical means are considered a magnifying lens or a telescope; however a video camera in the vicinity of the workpiece may also be provided together with a display device at a distance thereof.

Locking means for the workpiece carrier may be provided on the holding device to avoid unintentional displacement of the workpiece carrier relative to the holding device.

These locking means may consist of a spring chuck disposed on the holding device and a ball pivot attached to the workpiece carrier. Alternatively, the locking means could comprise two concentric conical surfaces, which would be disposed on one hand on the holding device on the other hand on the workpiece carrier. In this case, adjustment means are provided for loosening and tightening of the two conical surfaces.

The holding device is preferably provided with a shank wherein the device's locking means are arranged in such a manner that they may be accessed from the side opposite the clamping location.

In an additional embodiment, the workpiece carrier is provided with a diameter-adjusting, spring-loaded stud, whereas the holding device is provided with a receiving opening for the stud and wherein the stud is pressed together by its spring action in relation to its diameter in the installed condition. Thereby a friction lock is obtained, which prevents unintentional pivoting.

An embodiment example of the device according to the invention, together with various holding devices, is illustrated in the drawings.

BRIEF DESCRIPTION OF THE DRAWINGS

FIGS. 5 through 7 show a third workpiece carrier without a holding device;

DETAILED DESCRIPTION OF THE PREFERRED EMBODIMENTS

Figure 1:
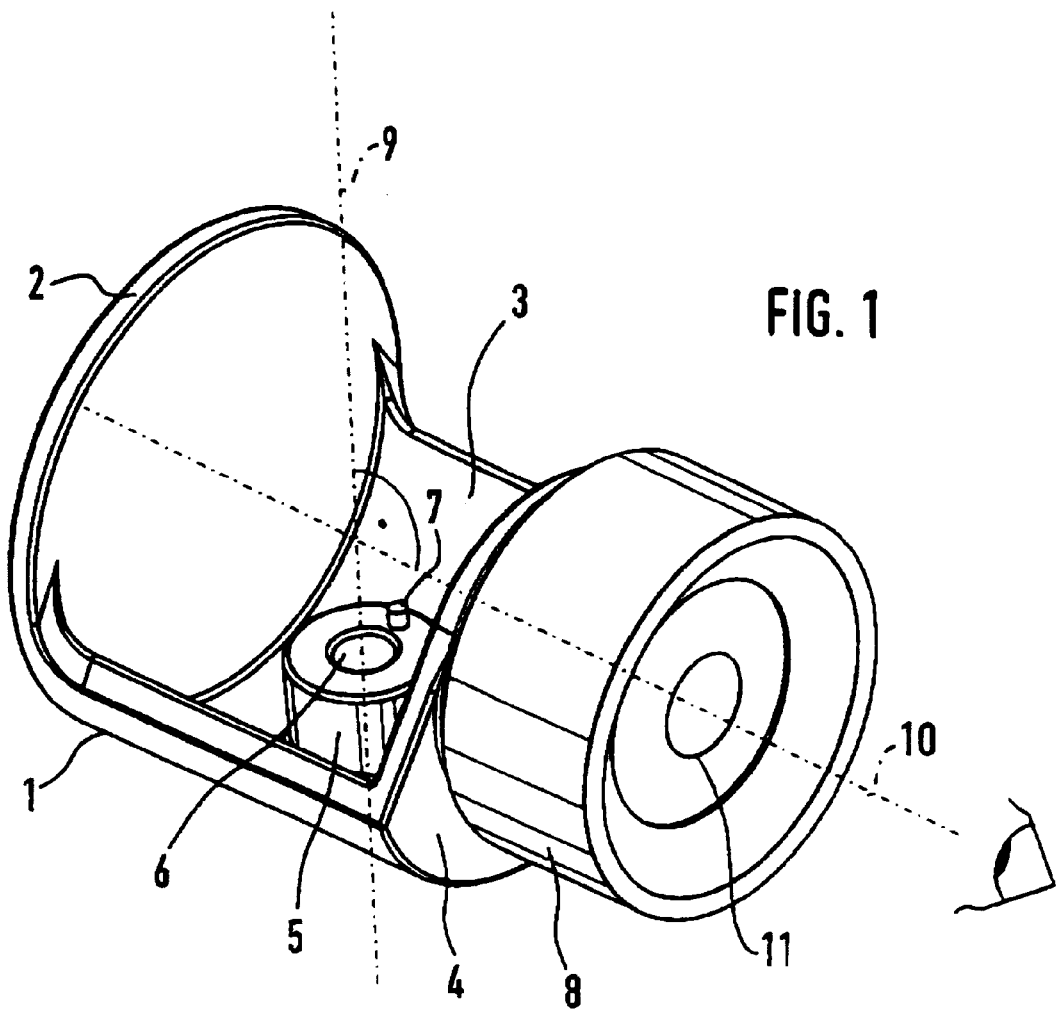
FIG. 1 shows the device for alignment and mounting without the interior holding device.

The device illustrated in FIG. 1 to align and mount a workpiece on a holding device is provided with an open housing 1, which consists of a base piece 2, a housing wall 3 and an objective lens holder 4. A receiving device 5 and a receiving opening 6 to receive a holding device (not illustrated) are arranged within the housing wall 3. The receiving device 5 is provided with means 7 for positioning determination of the holding device relative to the receiving opening 6 in the form of a stop 7 at which the holding device is securely held it its position.

In place of a stop 7 there can also be provided a scale, for example, on which a numerical value can be found, which is then transmitted to a measuring device (not illustrated).

A magnifying lens 8 is disposed in the objective lens holder 4 through which one can view the inside of the open housing 1.

The center axis, which leads through the receiving device 5, is perpendicular to the optical axis 10 of the optical means 8. There are alignment aids 11 proposed in form of concentric circles to avoid reading errors caused by oblique viewing.

To improve alignment, the housing base 2 may be made of transparent material or a mirror to transmit additional light into the inner housing and also to the workpiece that is to be aligned. Furthermore, the entire inner housing may have mirrors on all sides, including the inner side of the objective lens holder 4.

Figure 2:
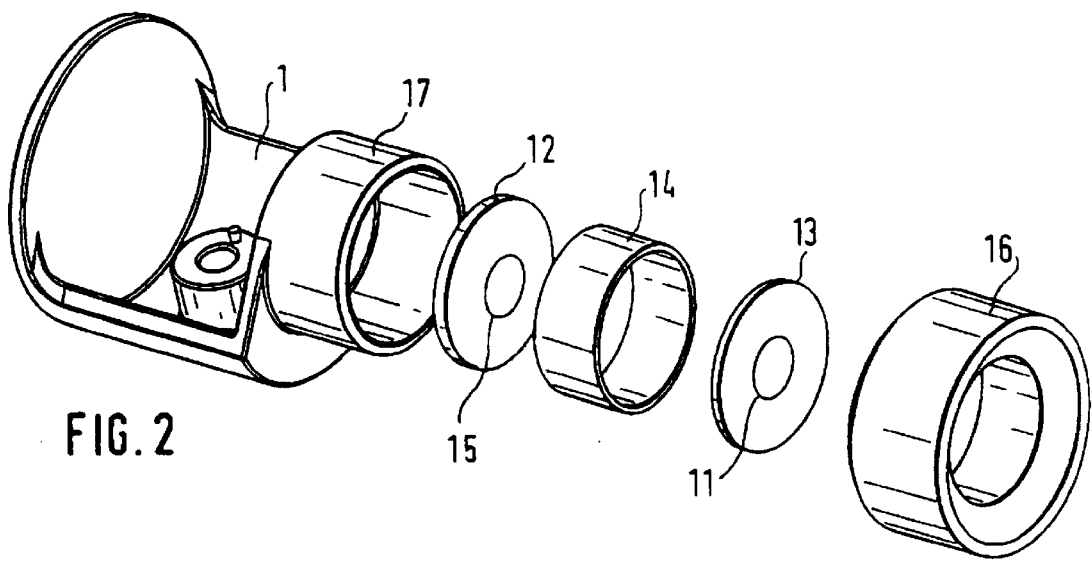
FIG. 2 depicts an exploded view of the device in Fig. 1.

FIG. 2 illustrates individual components of the device itself. The housing 1 is made in one piece and the optical means, including the magnifying lens 8, are illustrated as individual parts. Two lenses 12, 13 can be seen, which are arranged together with a spacer 14 at a specific distance from one another. The lenses 12, 13 are provided with alignment aids 11, 15 in the form of concentric circles, which must be aligned with one another to cover each other or must be at least concentrically aligned in order for the viewing axis to be correct. An end piece 16, which is fitted over the housing connection piece 17 is used to firmly connect individual components with the housing 1.

Figure 3:
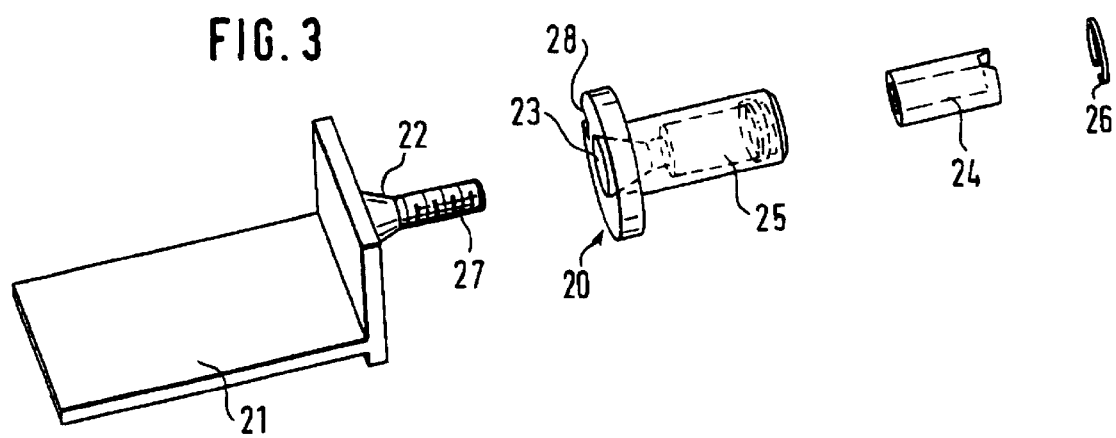
FIG. 3 shows a first holding device with a workpiece carrier.

In FIG. 3 there is a first holding device illustrated, which can receive a workpiece carrier 21 together with locking means and which can hold the workpiece carrier 21 firmly in its position. In addition, there is provided a concentric surface 22, 23 on the workpiece carrier 21 and the holding device 20, respectively, which may be tightened against each other by adjustment means 24 in the form of a screw nut.

The screw nut is positioned in the shank 25 of the holding device and is kept securely in place by a snap ring 26. The nut 24 is provided with inner threads which engage with the outer threads of the projecting part 27 of the workpiece carrier. The nut may tighten or free the conical surfaces by being rotated.

The workpiece carrier 21 itself may be made of synthetic material as a disposable item. The workpiece that is to be measured is glued onto the workpiece carrier 21 and is aligned by sight. The workpiece carrier 21 is subsequently inserted into the holding device 20. The holding device itself is then installed in the novel device and is firmly placed in its position by a recess 28. The recess 28 communicates with the projection 7 (FIG. 1). The exact position of the workpiece (not shown) arranged on the workpiece carrier 21 is now aligned by manual rotation relative to the holding device 20 in such a manner that all relevant (workpiece) surfaces may be optimally viewed without additional rotation of the holding device. Ideally, the insertion direction of the fitting body corresponds with the viewing direction of a fitting body as inserted into the workpiece, whereby the viewing direction is also the measuring direction.

Figure 4:
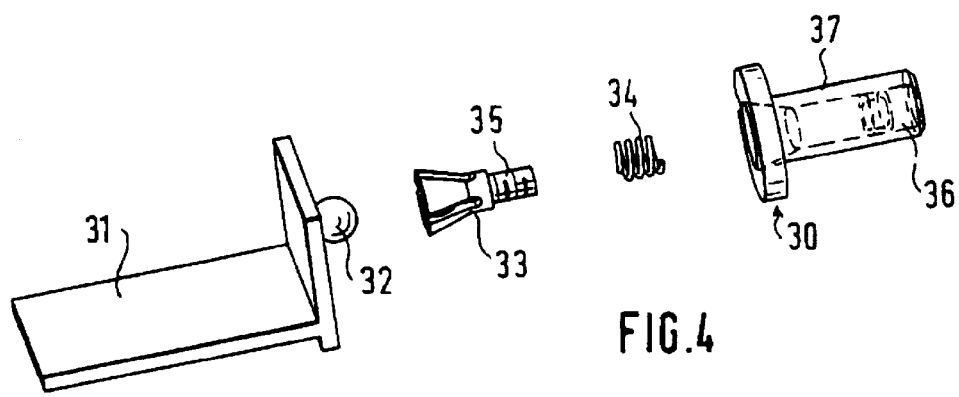
FIG. 4 shows a second holding device with a workpiece carrier.

In FIG. 4 there is illustrated an additional connection between a holding device 30 and a workpiece carrier 31. The workpiece carrier 31 is provided with a ball pivot 32, which may be engaged with a spring chuck 33 that is attached to the holding device. The spring chuck may be tensioned by a spring 34 that is disposed on a threaded segment whereby adjustment means 36 are provided in the shank 37.

The workpiece carrier illustrated in FIG. 5 through 7 can do without additional adjustment means; however, it is provided with a diameter-adjusting, spring-loaded stud 41. The stud 41 is provided with a longitudinal slot 42, which causes the diameter of the stud 41 to be enlarged in its uninstalled condition. Based on this slot, however, the stud can be tensioned during installation of the workpiece carrier 40 into a holding device, which is proved with a hollow shank, and the stud forms thereby a friction-locking connection by the force of the spring.

Figure 8:
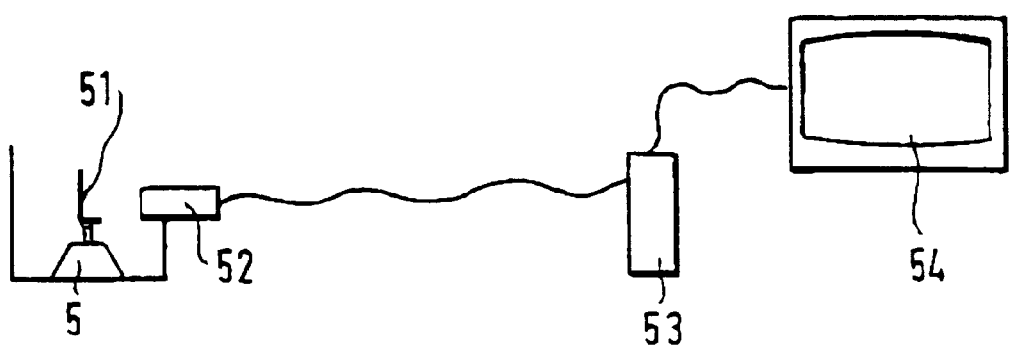
FIG. 8 shows a device with a video camera.

FIG. 8 shows a workpiece carrier 51 arranged on the receiving device 5 according to the invention onto which a video camera 52 is pointed. The video camera 52 supplies a signal that is interpreted by a central unit 53 and which is then shown on the display unit 54. It is also possible to attach this video camera arrangement to the device designed for additional processing of the workpiece whereby accessibility for manual alignment has to be made available. The great advantage of an independently manual device is the fact that with this device, independent from costly apparatuses, a number of workpieces may be aligned so that times for resetting is kept to a minimum. Furthermore, it is essential that not only one alignment of the workpiece takes place, but also the mounting (fastening) of the workpiece onto the workpiece carrier is feasible with the aid of optical means and that such an exact alignment is made possible already during the mounting process so that fine adjustment is also possible subsequently.

Figure 9:
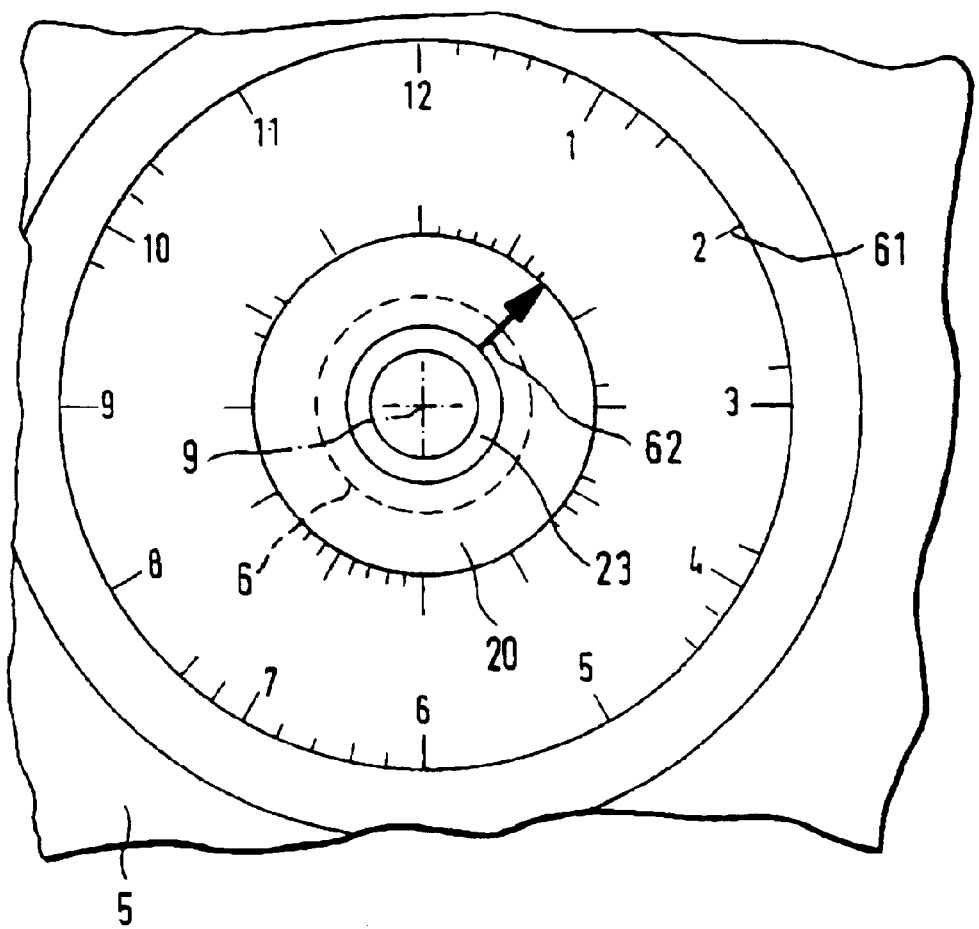
FIG. 9 shows a scale as means for determining the selected position of the holding device.

In FIG. 9 there is a holding device 20 (as illustrated in FIG. 3) that is inserted into the receiving device 5 whereby the receiving device 5 is provided with a scale 61, which communicates with a marker 62 that is attached to the holding device 20. In a top view one can see furthermore the tension cone 23 of the holding device 20 as well as the receiving opening 6 to receive the holding device 20, illustrated by a dotted line. The scale 61 is concentric relative to the center axis 9 so that during rotation of the holding device 20, the marker 62 is moved along the scale 61. In a holding device 20 of this type it is sufficient if the workpiece carrier (as a disposable item) is clamped tightly in the holding device 20 and is not further rotated relative to the holding device during the alignment in the novel device and in the measuring device. The alignment of the workpiece to be measured in relation to the center axis 9 is performed exclusively by rotation of the holding device 20 in the receiving device 5 whereby—after successful alignment—the scale value is determined as indicated by the marker attached to the holding device 20 and this scale value is used in the alignment of the measuring device. The measuring device has also a scale in this case so that the holding device can be placed in the same position as the device according to the invention. To prevent unintentional rotation of the holding device in the novel device, after the alignment and before the (scale) reading, locking means may be provided, which can be designed as an O-ring or be made from elastic material. By corresponding over-sizing of the O-ring, a sufficient friction lock is obtained, which prevents unintentional rotation and which allows at the same time relative effortless insertion and removal of the holding device.

Should a holding device 20 be provided with a scale and a stop that cooperates with an counter-stop, then it is sufficient if the novel device is provided exclusively with a scale whereby the holding device 20 is then securely placed in position in the measuring device by means of a thereto arranged stop and its counter-stop. By entering the value read from the scale on the holding device into a control unit of the measuring device, the holding device is rotated around its center axis corresponding to the value so that measuring is conducted in the same direction as the direction of alignment of the workpiece in the device according to the invention.

The use of the device according to the invention is described below. The workpiece that is to be measured is trimmed to a specific size. Then the holding device, which is aligned in the measuring direction, is inserted into the novel device together with its movably arranged workpiece carrier onto which the model has been placed.

The workpiece is roughly aligned by using the optical means for viewing and it is subsequently glued down. Afterwards, the holding device and the workpiece carrier are finely adjusted to one another again by using the optical means and then the workpiece carrier is fixed in relation to the holding device. Fine adjustment is performed thereby in case of measuring a cavity of a tooth to produce a fitting body so that the insertion axis of the workpiece is moved in a pre-defined direction. By fixing the workpiece carrier relative to the holding device, it is possible to remove the holding device from the novel device and to insert it in the same position as the measuring axis into the measuring device for measurement.

A substantial area of application for the present invention is the use of the device in the preparation of measuring a tooth in a combined measuring and grinding apparatus. It is important hereby that the workpiece to be measured and the blank for the workpiece that is to be shaped by grinding are processed one after the other in the same receiving device. The measuring device can furthermore be attached to a spindle that is equipped with a grinding tool, which is already well known in the state-of-the-art.

We claim:

1. A combination of an apparatus for viewing a workpiece, a carrier for the workpiece, and a holding device for the carrier;

said carrier including a base having a first part on which a workpiece is positionable and a second part, and a projection which extends away from said second part of said base, said holding device being rotatable and connectable to said projection of said carrier, locking means for locking said holding device to said carrier, and said apparatus for viewing a workpiece comprising means defining a circular opening in which said holding device is positionable, positioning means adjacent said opening to determine the rotational positioning of said holding device in said opening, and optical means for viewing a workpiece on a carrier connected to said holding device.

2. A combination according to claim 1, wherein said apparatus includes optical means arranged on an axis perpendicular to a center axis of said holding device.

3. A combination according to claim 1, wherein the optical means are provided with at least two alignment aids.

4. A combination according to claim 3, wherein the alignment aids along a center axis of said optical means are concentric circles disposed at a distance from one another.

5. A combination according to claim 3, wherein said optical means comprise a magnifying lens or a telescope.

6. A combination according to claim 3, wherein said optical means comprise a video camera that is arranged in the vicinity of the carrier and a display apparatus located remotely thereof.

7. A combination according to claim 1, wherein the locking means comprise a spring chuck disposed in the holding device and a ball pivot attached to the carrier.

8. A combination according to claim 1, wherein the locking means comprise two concentric conical surfaces which are disposed on the holding device on one hand and on the carrier on the other, and wherein adjustment means are provided for loosening and tightening of the two conical surfaces.

9. A combination according to claim 1, wherein said holding device is provided with a shank, wherein the locking means are arranged within said shank, and wherein said locking means is accessible from a side of the holding device opposite the carrier.

10. A combination according to claim 1, wherein the locking means comprises a diameter-adjusting, spring-loaded stud on said carrier and a receiving opening in said holding device for said stud, whereby said stud is pushed together by spring action in its installed condition in said holding device in relation to a diameter thereof.

11. A combination according to claim 1, wherein said second part of said carrier is generally perpendicular to said first part.

\* \* \* \* \*